US006960168B2

(12) United States Patent
Yanagidaira et al.

(10) Patent No.: US 6,960,168 B2
(45) Date of Patent: Nov. 1, 2005

(54) SYSTEM FOR INFORMING OF DRIVER'S MENTAL CONDITION

(75) Inventors: Masatoshi Yanagidaira, Tsurugashima (JP); Mitsuo Yasushi, Tsurugashima (JP)

(73) Assignee: Pioneer Corporation, Tokyo (JP)

( * ) Notice: Subject to any disclaimer, the term of this patent is extended or adjusted under 35 U.S.C. 154(b) by 0 days.

(21) Appl. No.: 10/455,726

(22) Filed: Jun. 6, 2003

(65) Prior Publication Data

US 2004/0002638 A1    Jan. 1, 2004

(30) Foreign Application Priority Data

Jun. 27, 2002  (JP)  ............................. 2002-188285

(51) Int. Cl.[7] ................................................ A61B 5/00
(52) U.S. Cl. ...................................... 600/300; 128/920
(58) Field of Search ............................... 600/300–301, 600/485, 490, 500, 508, 549; 128/903, 904, 128/920–925; 340/425; 701/201

(56) References Cited

U.S. PATENT DOCUMENTS

| 4,706,072 A | 11/1987 | Ikeyama | ..................... 340/576 |
| 6,599,243 B2 * | 7/2003 | Woltermann et al. | ....... 600/300 |

FOREIGN PATENT DOCUMENTS

| EP | 0 713 675 | 5/1996 |
| JP | 8-140949 | 6/1996 |
| WO | WO 96/16830 | 6/1996 |
| WO | WO 00/44580 | 8/2000 |

* cited by examiner

Primary Examiner—Max F. Hindenburg
Assistant Examiner—Michael C. Astorino
(74) Attorney, Agent, or Firm—Morgan Lewis & Bockius LLP (57) ABSTRACT

A driver mental condition information system in which physiological data of the driver of a vehicle is detected and the mental condition of the driver is calculated as a mental condition evaluation value in accordance with the physiological data, thereby indicating the mental condition of the driver, using the mental condition evaluation value along with a threshold value.

12 Claims, 11 Drawing Sheets

| DRIVER | TIME DATA | | VEHICLE DATA | | | PHYSIOLOGICAL DATA | | | MENTAL CONDITION | | | TRAFFIC CONDITION |
|---|---|---|---|---|---|---|---|---|---|---|---|---|
| | DATE | TIME | LOCATION | SPEED | ELAPSED TIME | HEARTBEAT RATE | HEARTBEAT FLUCTUATION | RESPIRATORY RATE | SLEEPINESS | FATIGUE | STRAIN | |
| A | MARCH 3 | 18:00 | COORDI-NATES | 100km | 60 MIN. | 65 | 10 | 15 | 3 | 2 | 1 | HIGHWAY |
| ------ | ------ | ------ | ------ | ------ | ------ | ------ | ------ | ------ | ------ | ------ | ------ | ------ |

FIG. 14

| DRIVER | | HEARTBEAT RATE | PHYSIOLOGICAL DATA | | MENTAL CONDITION | | |
|---|---|---|---|---|---|---|---|
| | | | HEARTBEAT FLUCTUATION | RESPIRATORY RATE | SLEEPINESS | FATIGUE | STRAIN |
| A | MAXIMUM VALUE | | | | | | |
| | AVERAGE VALUE | | | | | | |
| | MINIMUM VALUE | | | | | | |
| B | MAXIMUM VALUE | | | | | | |
| | AVERAGE VALUE | | | | | | |
| | MINIMUM VALUE | | | | | | |
| C | MAXIMUM VALUE | | | | | | |
| | AVERAGE VALUE | | | | | | |
| | MINIMUM VALUE | | | | | | |

SYSTEM FOR INFORMING OF DRIVER'S MENTAL CONDITION

BACKGROUND OF THE INVENTION

1. Field of the Invention

The present invention relates to a driver mental condition information system for informing of a driver's mental condition.

2. Description of the Related Background Art

Systems for providing the driver of a vehicle with information on a driver's mental condition such as sleepiness and fatigue are known (e.g., Japanese Patent Kokai No. 8-140949). In such a conventional driver mental condition information system, physiological data of a driver is detected, and a mental condition of the driver is then converted into a numerical value in accordance with the physiological data detected to compare the numerical value with a threshold value, thereby determining whether the mental condition of the driver has become too poor to assure the safe operation of a vehicle due to sleepiness, fatigue or the like. If the mental condition of the driver is determined to have become too poor, a warning is issued to the driver by means of a lamp or sound.

However, the conventional system has been designed to present only binary information that allowed a warning to be issued when the numerical value indicative of the mental condition of the driver exceeded the threshold value. Thus, there is a problem that the system is not able to precisely inform of the driver's mental condition that varied every moment.

SUMMARY OF THE INVENTION

It is therefore an object of the present invention to provide a driver mental condition information system that can precisely inform of the driver's mental condition to the driver and a method thereof.

A driver mental condition information system according to the present invention comprises a physiological data detector which detects physiological data of a driver of a vehicle, a mental condition calculator which calculates a mental condition of the driver as a mental condition evaluation value in accordance with the physiological data, an evaluation threshold value setting device which sets a threshold value for evaluating the mental condition of the driver, and an indicator which indicates the mental condition of the driver using the mental condition evaluation value along with the threshold value.

A method for displaying a driver's mental condition according to the present invention comprises detecting physiological data of a driver of a vehicle, calculating a mental condition of the driver as a mental condition evaluation value in accordance with the physiological data, setting a threshold value for evaluating of the mental condition of the driver, and indicating the mental condition of the driver using the mental condition evaluation value along with the threshold value.

DETAILED DESCRIPTION OF THE INVENTION

The present invention will be described below in more detail with reference to the accompanying drawings in accordance with the embodiment.

Figure 1:
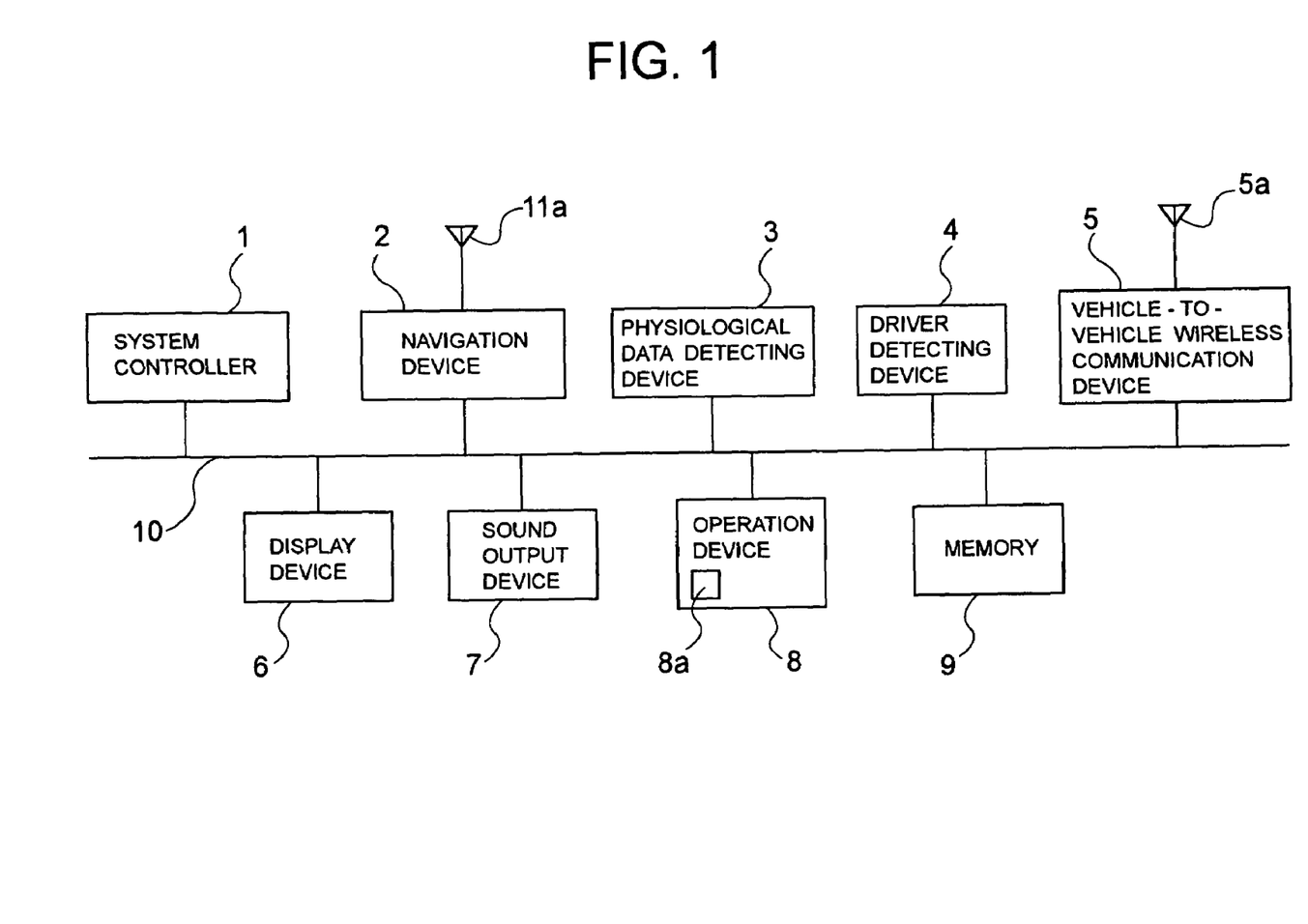
FIG. 1 is a block diagram showing an embodiment of the present invention.

FIG. 1 is a view showing a driver mental condition information system according to the present invention. The driver mental condition information system comprises a system controller 1, a navigation device 2, a physiological data detecting device 3, a driver detecting device 4, a vehicle-to-vehicle wireless communication device 5, a display device 6, a sound output device 7, an operation device 8, and a memory 9. The system controller 1, the navigation device 2, the physiological data detecting device 3, the driver detecting device 4, the vehicle-to-vehicle wireless communication device 5, the display device 6, the sound output device 7, and the operation device 8 are connected to each other via a system bus 10.

The system controller 1 comprises for example, a microcomputer for controlling the entire system. The navigation device 2 basically detects a current location of a vehicle in which the system is mounted and allows a map of a surrounding area including the current location to be displayed on the display device 6, thereby providing the driver and a passenger with route guidance for traveling from the current location to a desired destination.

Figure 2:
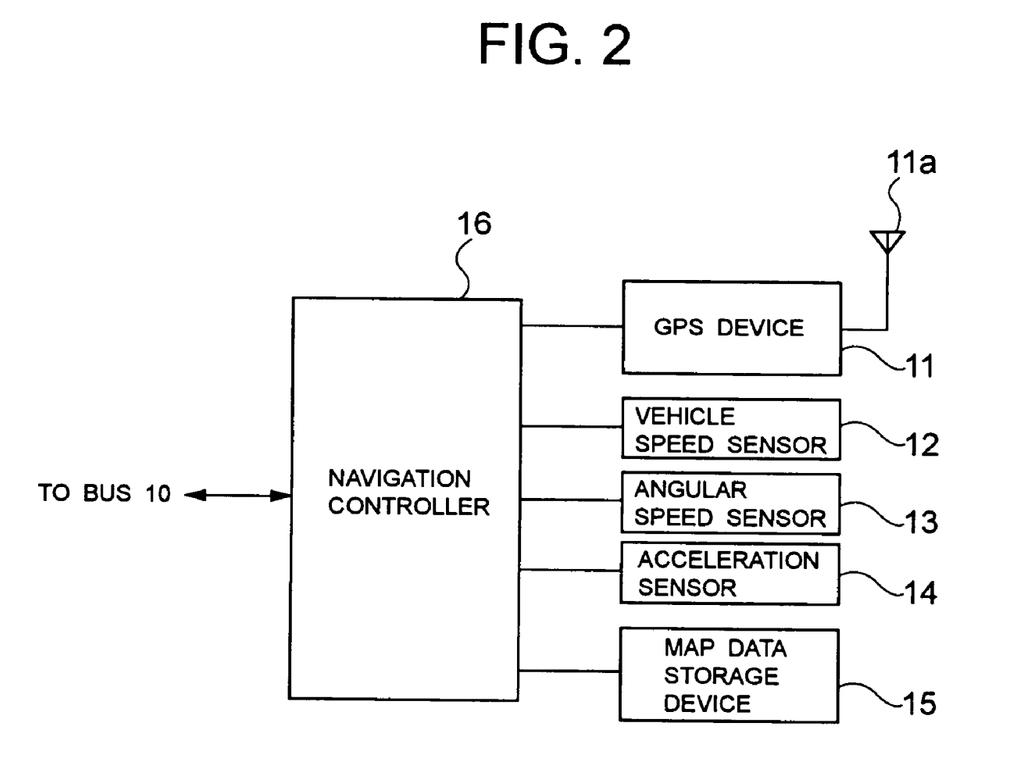
FIG. 2 is a block diagram showing the configuration of the navigation device provided in the system of FIG. 1.

As shown in FIG. 2, the navigation device 2 includes a GPS (Global Positioning System) device 11, a vehicle speed sensor 12, an angular speed sensor 13, an acceleration sensor 14, a map data storage device 15, and a navigation controller 16. The GPS device 11 connected to a GPS antenna 11a receives at the antenna 11a radio waves transmitted from satellites, and computes the GPS vehicle self-location data, which contains a current location and a traveling direction of the vehicle, based on the received signal. The vehicle speed sensor 12, the angular speed sensor 13, and the acceleration sensor 14 are self-contained sensors for detecting vehicle data such as on a location and a traveling direction of the vehicle without obtaining information from outside the vehicle. The vehicle speed sensor 12 detects a speed of the vehicle. The angular speed sensor 13 detects an angular speed of the vehicle. The acceleration sensor 14 detects an acceleration of the vehicle. The map data storage device 15 is a drive unit for storage media such as DVD and reads information data such as map data pre-stored on the storage media. Te navigation controller 16 is connected to the GPS device 11, the vehicle speed sensor 12, the angular speed sensor 13, the acceleration sensor 14, and the map data storage device 15 to control the entire navigation system. The navigation device 2 also generates information on current time.

The physiological data detecting device 3 detects the number of heartbeats of the driver and then outputs physiological data indicative of the number of heartbeats. The physiological data detecting device 3 detects the conduction state of electrodes and the potential difference therebetween when the driver grips the steeling wheel of the vehicle, thereby providing the physiological data.

Figure 3:
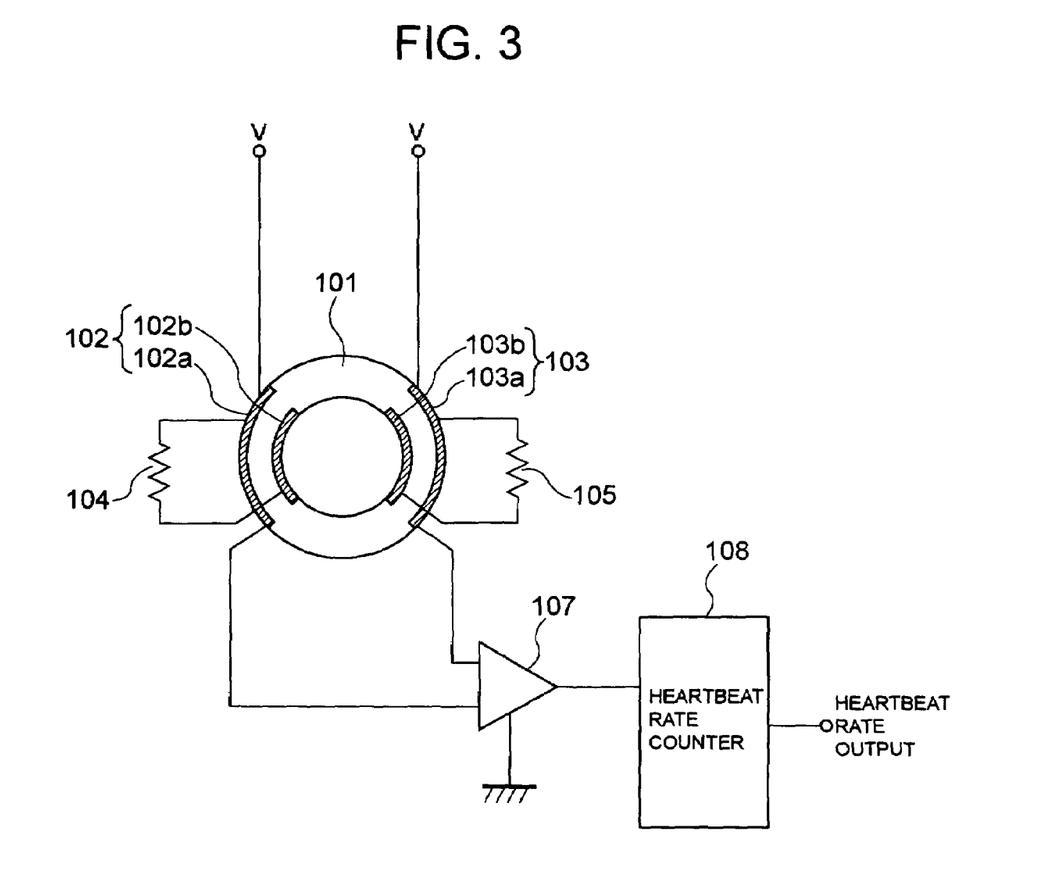
FIG. 3 is a block diagram showing the configuration of the physiological data sensor provided in the system of FIG. 1.

As shown in FIG. 3, the physiological data detecting device 3 is provided with a pair of electrodes 102a, 102b, generally denoted by 102, and a pair of electrodes 103a, 103b, generally denoted by 103. The electrodes 102 are each separately installed on the outer and inner positions on the left side of a steering wheel 101, where the driver places his or her left hand. The electrodes 103 are each separately installed on the outer and inner positions on the right side of the steering wheel 101, where the driver places his or her right hand. The electrodes 102a, 103a are individually supplied with the same constant current at a terminal V from a power source (not shown), while although not illustrated, the electrodes 102b, 103b are both connected to the ground. When the driver grips the electrodes, a left-hand skin resistance 104 is inserted between the electrodes 102a, 102b, which constitute the left-hand electrodes 102, and a right-hand skin resistance 105 is inserted between the electrodes 103a, 103b, which constitute the right-hand electrodes 103. The potentials at the electrodes 102a, 103a are each supplied to a differential amplifier 107. The differential amplifier 107 amplifies the potential difference between both the electrodes and then outputs a heartbeat signal at a limited frequency band. The heartbeat signal is supplied to a heartbeat rate counter 108. The heartbeat rate counter 108 counts the number of heartbeats (heartbeat rate) as physiological data in accordance with the heartbeat signal.

For the heartbeat detection, the peripheral bloodstream in a hand placed on the steering wheel is detected with an optical sensor installed at the steering wheel using so-called pulse waves. Alternatively, the heart can be irradiated with weak microwaves generated by a high frequency circuit installed in a seat belt or the like to analyze the difference between the irradiation signal and its return signal, thereby measuring heartbeats.

The number of heartbeats usually increases in a nervous or irritating condition. A change in these conditions can be judged in accordance with an electrocardiography to thereby evaluate the mental condition of the driver. Alternatively, it is also possible to employ a method by which spectrum variations in the variation components of heartbeat intervals are analyzed for evaluation. Furthermore, using skin resistance, perspiration or the electrodermal reaction (different from the electrocardiography) between the right and left hands can also be examined, thereby judging the mental condition. The driver's mental condition can be thus grasped with higher accuracy in combination with the electrodermal reaction indicative of a temporary tension. Where applicable, it is also possible to employ a technique that can provide physiological data other than those mentioned above.

The driver detecting device 4 is a sensor for detecting information on a driver to identify the driver. For example, the driver detecting device 4 detects a parameter by which the driver is identified, such as the voice pattern, iris, or fingerprint of the driver. The driver detection data indicative of the driver's parameter is supplied to the system controller 1 via the system bus 10.

The vehicle-to-vehicle wireless communication device 5, provided to communicate with other vehicles, transmits and receives radio signals via an antenna 5a. For example, information in the radio signal transmitted contains vehicle ID information for identifying the vehicle, driver information indicative of the driver, data on a current location and a traveling speed of the vehicle, and sleepiness information. The data to be sent is supplied from the system controller 1 to the vehicle-to-vehicle wireless communication device 5 via the system bus 10, while the data received at the vehicle-to-vehicle wireless communication device 5 is supplied from the vehicle-to-vehicle wireless communication device 5 to the system controller 1 via the system bus 10. It is possible to utilize an on-board telephone or a cellular phone as the vehicle-to-vehicle wireless communication device 5.

The display device 6 is for example, a liquid crystal display device, displays information instructed by the system controller 1 or the navigation device 2. Although detailed later, the information to be displayed includes a map, levels of sleepiness, a red zone, and a warning indication.

The sound output device 7 issues a warning sound in response to an instruction from the system controller 1. The operation device 8 receives an operational input provided by a user such as a driver. The operation device 8 is provided with a setting switch 8a which the driver operates to generate a sleepiness setting request signal and send it to the system bus 10. The drowsy driver will depress the setting switch 8a.

The system controller 1 provides operational control to the memory 9 to store a variety of data therein.

The operation of the driver mental condition information system configured as described above is explained below.

Figure 4:
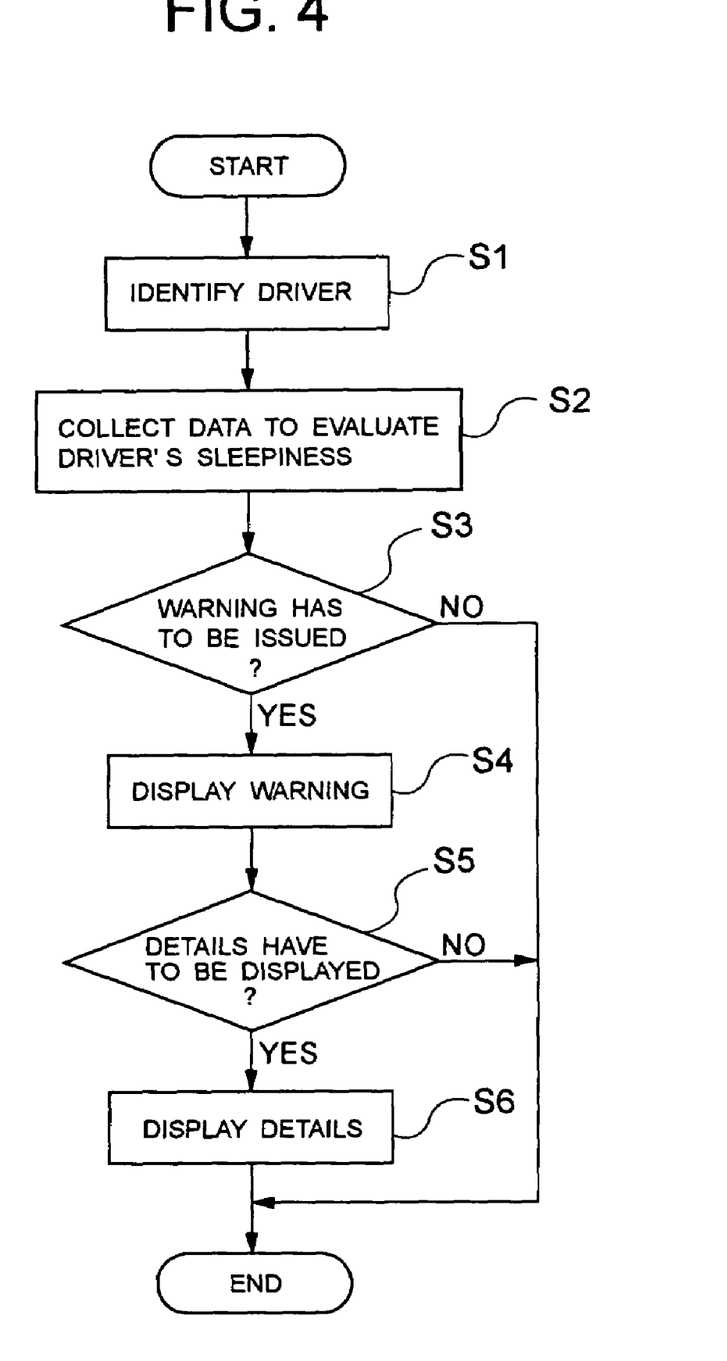
FIG. 4 is a flowchart showing the main operation of a system controller.

When a driver starts driving the vehicle, the system controller 1 identifies the driver as shown in FIG. 4 (step S1). In step S1, a determination is made in accordance with the driver detection data output from the driver detecting device 4. That is, if the driver parameters available to identify the driver have already been registered, the associated driver is identified in accordance with the driver detection data. An unregistered driver has to input his or her name at the operation device 8 to be identified.

After step S1 has been completed, the system controller 1 collects map data and navigation data from the navigation device 2 and physiological data from the physiological data detecting device 3 to perform a sleepiness evaluation operation (step S2). In the sleepiness evaluation operation, a sleepiness evaluation value Pn is calculated in accordance with the physiological data to determine whether the sleepiness evaluation value Pn is greater than a sleepiness evaluation threshold value SN to fall within a red zone. Further information on the sleepiness evaluation operation can be found in Japanese Patent Kokai No. 8-140949, and will not be detailed herein. However, a method for calculating the sleepiness evaluation value Pn is not limited to the one disclosed in Japanese Patent Kokai No. 8-140949, but any other methods can also be employed.

Following the sleepiness evaluation operation, if the system controller 1 determines in step S2 that the sleepiness evaluation value Pn is greater than the sleepiness evaluation threshold value SN which is the border value of the red zone, the controller 1 judges that a sleepiness warning should be issued (step S3). Therefore, since the sleepiness evaluation value Pn is a value in the red zone, a warning is displayed on the display device 6 (step S4).

Figure 5:
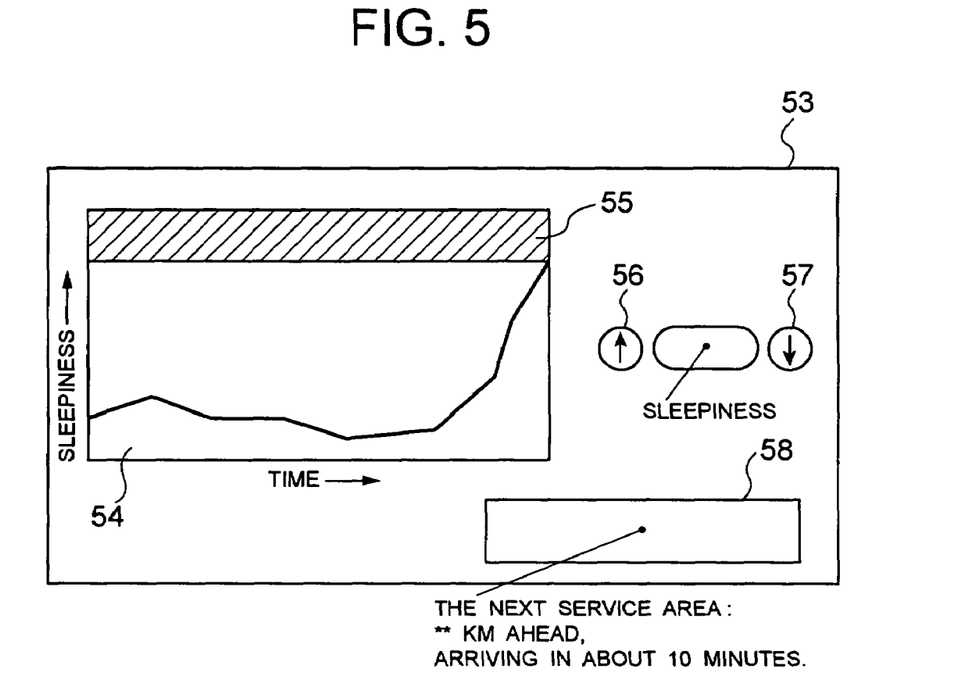
FIG. 5 is a view showing an example of displaying a sleepiness warning.

FIG. 5 is a view showing an example of a mental condition display window displayed on the display device 6. Within a window frame 53 on the display window, variations in the driver sleepiness evaluation value with time are shown in a graph 54 while a red zone 55 for the driver is also shown at the same time. The display is presented so that up/down correction buttons 56, 57 displayed or the operation device 8 can be operated to adjust the range of the red zone 55 or the sleepiness evaluation threshold value SN. Additionally, brief traffic information 58 is also displayed within the window frame 53. The mental condition display window may be displayed beside a usual navigation window or switched over to a navigation window or vice versa through an operation at the operation device 8. The display window makes it possible for the driver to grasp variations in his or her own mental condition during driving.

The warning displayed in step S4 on such a mental condition display window shows that the graph 54 representing the sleepiness evaluation value falls within the range of the red zone 55 as shown in FIG. 5, while the warning is presented visibly and audibly in a predetermined form. On the other hand, traffic information on the route to the nearest service area is displayed in a window for the traffic information 58. With the mental condition display window not being displayed on the display device 6, the process may provide control such that the mental condition display window is forcedly displayed on the display device 6.

Figure 6:
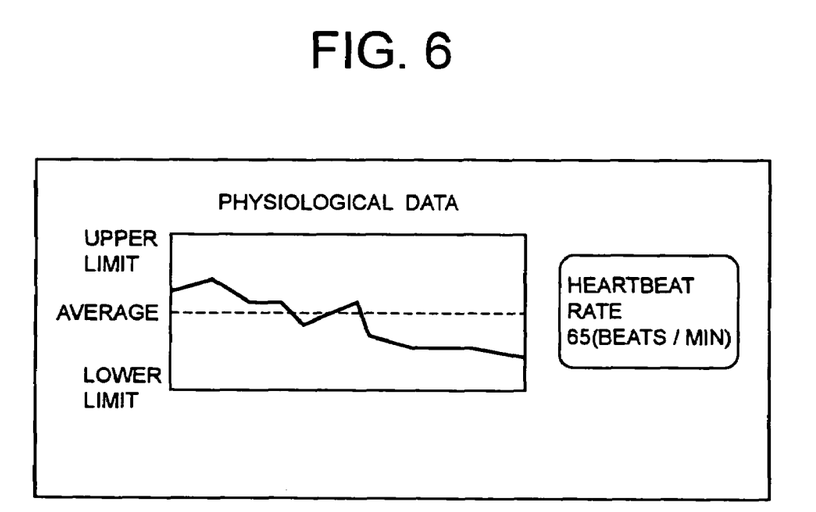
FIG. 6 is a view showing an example of displaying details.

The system controller 1 also determines whether details have to be displayed (step S5). For example, if the driver operates the operation device 8 to require details to be displayed, the system controller 1 determines that the details have to be displayed. When the details have to be displayed, the process reads out the maximum value, an average value, and the minimum value of the sleepiness evaluation value Pn from a predetermined area in the memory 9 to display the details (step S6). For example, the details to be displayed include variations in physiological data (heartbeat rate) and its average value, which are indicated in the graph as shown in FIG. 6. In the details displayed, also included is the current heartbeat rate.

The operation for adjusting the red zone 55 is described below. The system controller 1 executes a red zone adjustment routine while displaying a warning. The description will be given to a case where adjustments are made by means of the up/down correction buttons 56, 57 displayed. The operations carried out by the driver on the up/down correction buttons 56, 57 are individually detected by means of a touch switch (not shown), and the detected contents are supplied to the system controller 1 via the system bus 10.

Figure 7:
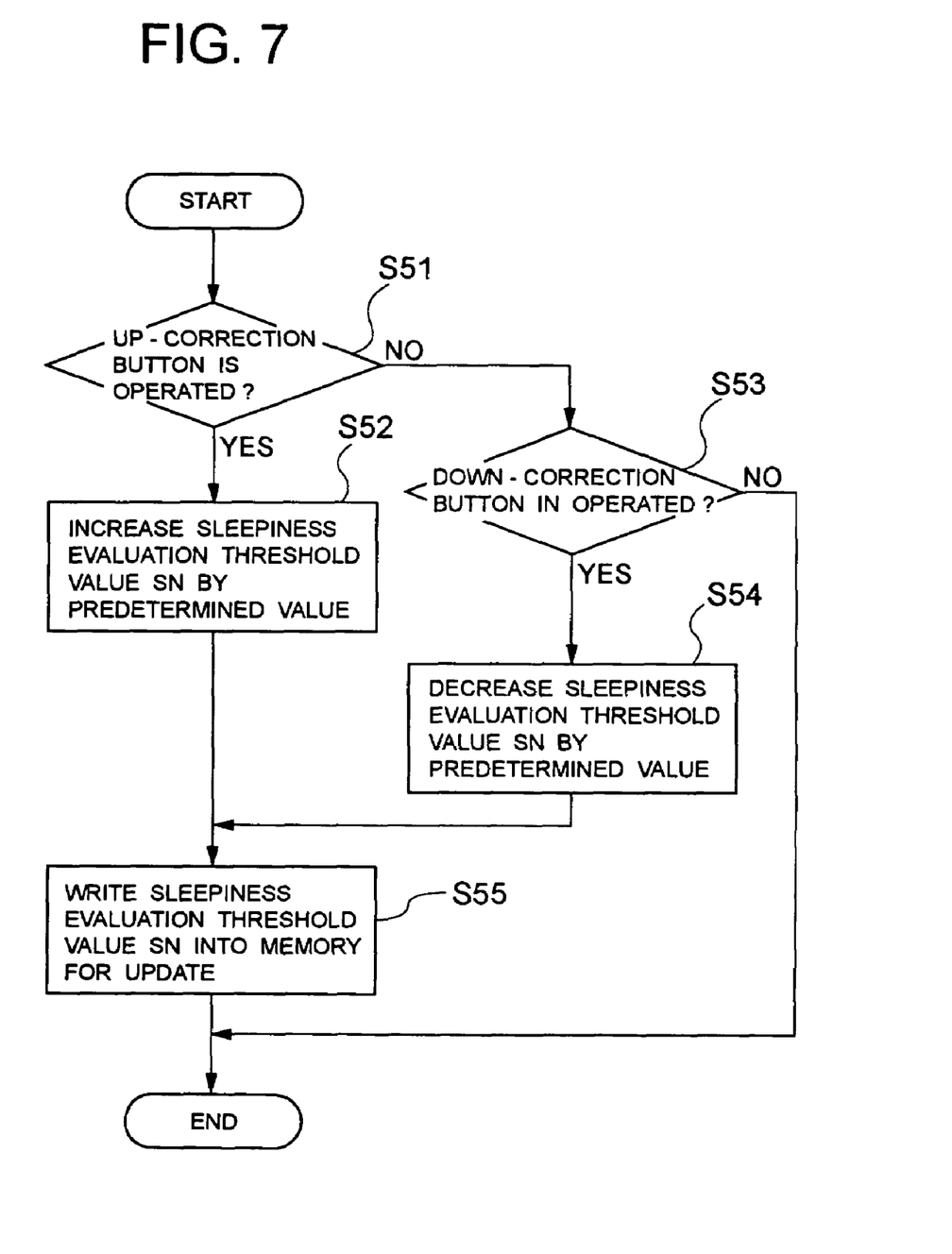
FIG. 7 is a flowchart showing a red zone adjustment routine.

As shown in FIG. 7, in the red zone adjustment routine, the process first determines whether the up correction button 56 has been operated (step S51). If the up correction button 56 has been operated, the sleepiness evaluation threshold value SN of the driver is increased by a predetermined value (e.g., one)(step S52). On the other hand, if the up correction button 56 has not been operated, the process determines whether the down correction button 57 has been operated (step S53). If the down correction button 57 has been operated, the sleepiness evaluation threshold value SN of the driver is decreased by a predetermined value (step S54). After step S52 or S54 has been completed, the sleepiness evaluation threshold value SN is written into the memory 9 for update (step S55). The sleepiness evaluation threshold value SN is that of the driver identified in step S1, and the sleepiness evaluation threshold value SN of the driver identified in step S1 is updated in step S55.

The processing in the red zone adjustment routine allows the sleepiness evaluation threshold value SN to be properly set for each driver. This enables a warning to sleepiness to be issued to each driver at a proper timing.

The operation device 8 can also be operated so that the red zone adjustment routine is executed at a desired point in time.

Figure 8:
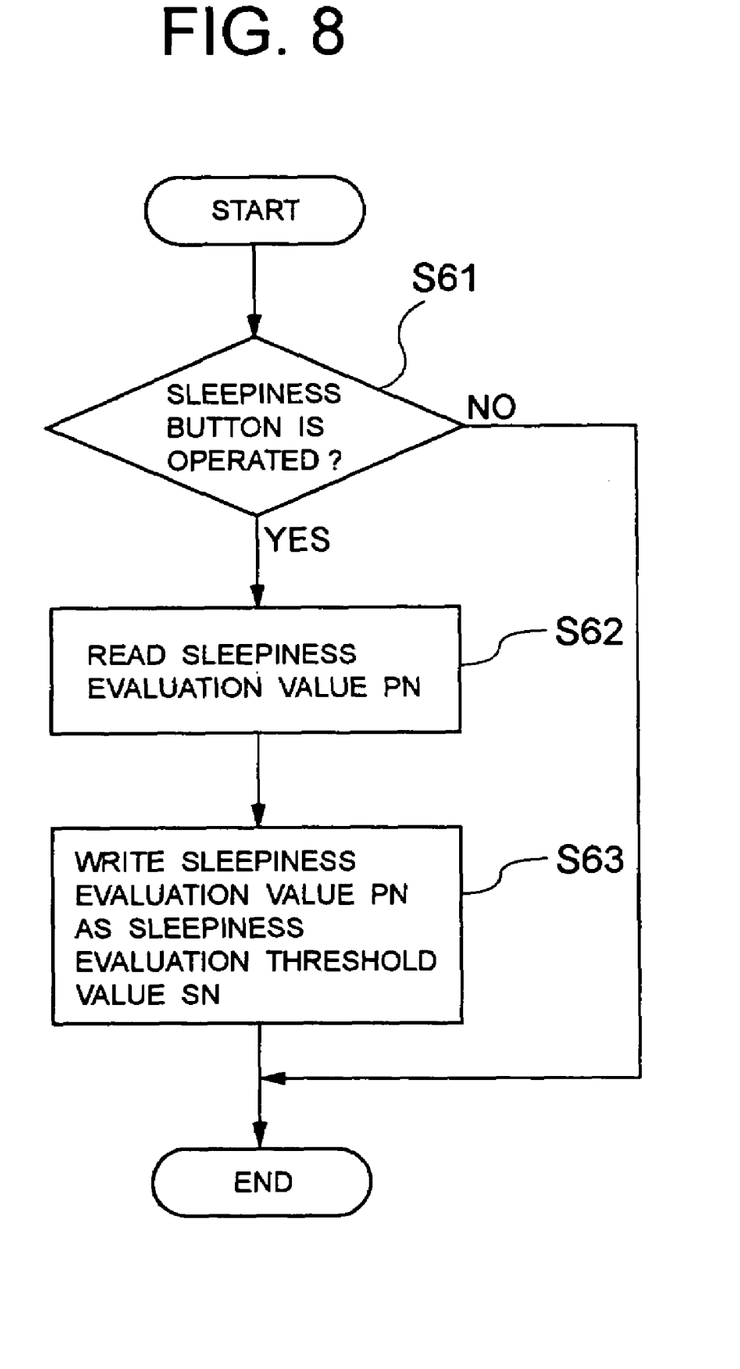
FIG. 8 is a flowchart showing a red zone setting routine.

To determine a sleepiness evaluation threshold value SN for each driver, the driver can operate a predetermined button (e.g., a sleepiness button, described below) at the operation device 8 when the driver actually feels sleepy, such that the sleepiness evaluation value Pn at that time point is employed as the sleepiness evaluation threshold value SN. As shown in FIG. 8, with the sleepiness button provided on the operation device 8, the system controller 1 determines whether the sleepiness button has been operated (step S61). If the sleepiness button has been operated, the process reads out a sleepiness evaluation value Pn stored in the memory 9 (step S62), and then writes the sleepiness evaluation value Pn in the memory 9 as a sleepiness evaluation threshold value SN (step S63).

Figure 9:
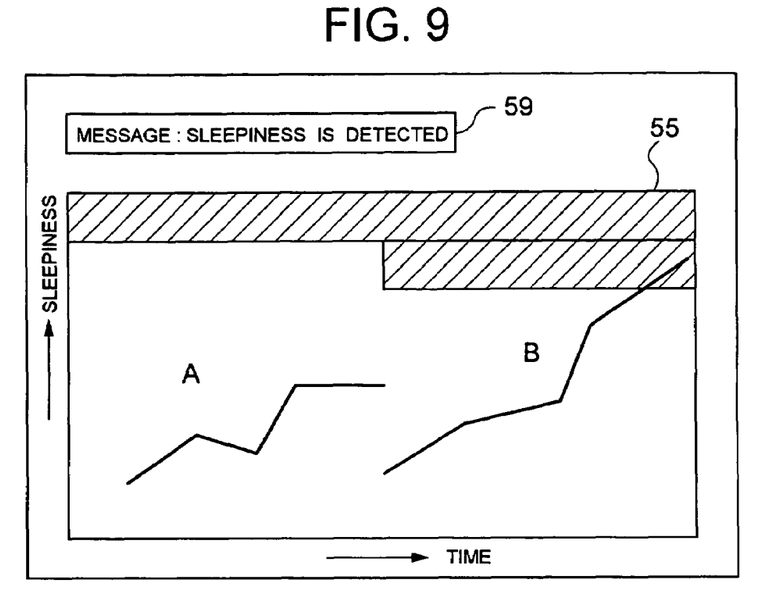
FIG. 9 is a view showing an example of displaying a sleepiness warning.

In step S4, the warning can be displayed as shown in FIG. 9. The example of displaying the warning, as illustrated in FIG. 9, shows that a driver "B" drove the same vehicle after a driver "A" had driven it. In this example, information on variations in the sleepiness evaluation values Pn of the drivers A, B is plotted in conjunction with the display of their red zones 55 as well as a message 59, "Sleepiness is detected."

Figure 10:
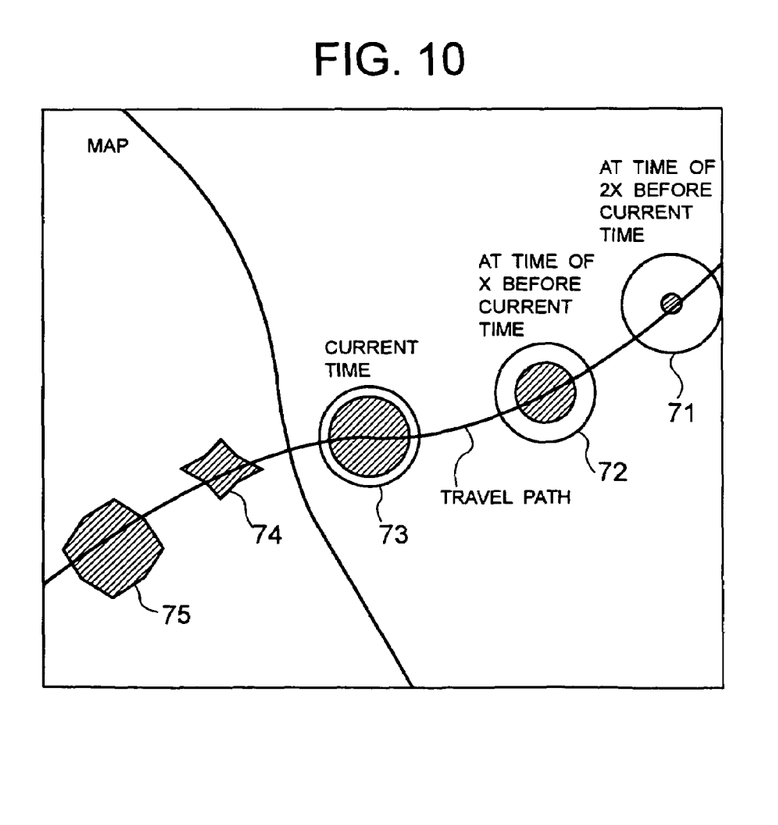
FIG. 10 is a view showing an example of displaying a sleepiness warning.
Figure 11:
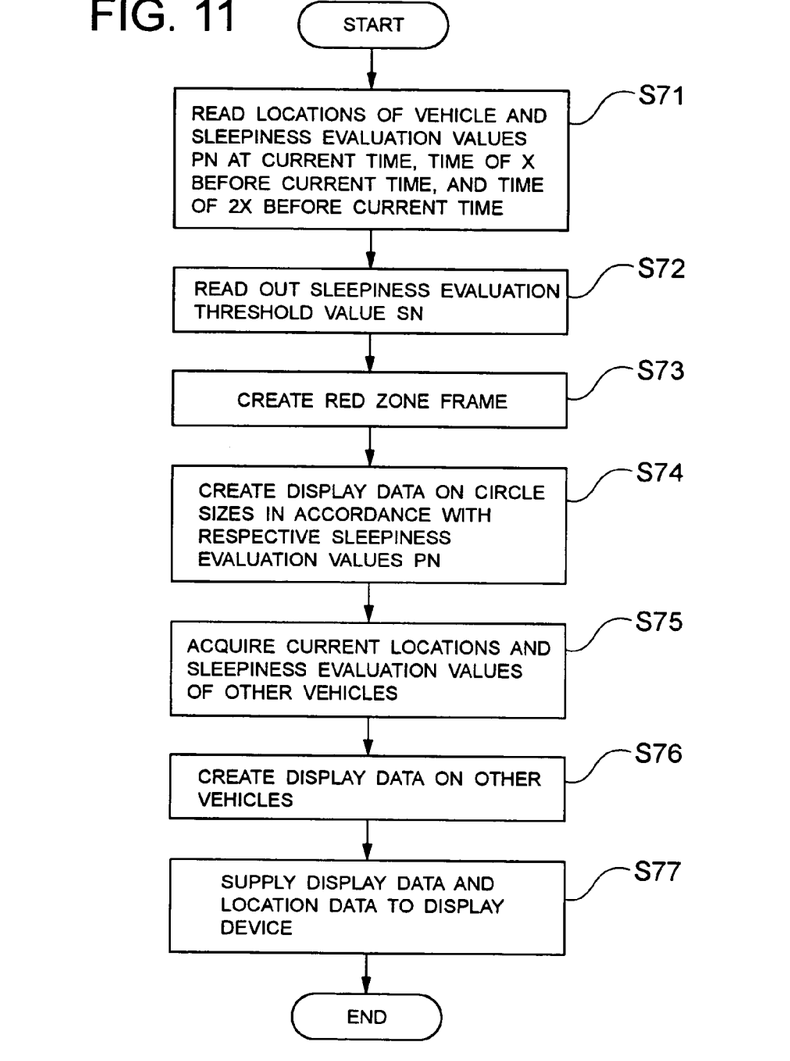
FIG. 11 is a flowchart showing an operation for displaying the sleepiness warning of FIG. 10.
Figure 12:
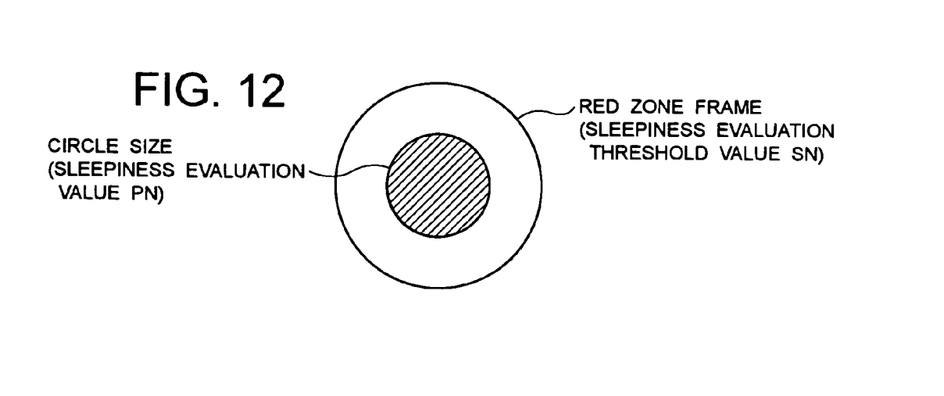
FIG. 12 is an explanatory view showing a marker in the display of the sleepiness warning of FIG. 10.

As shown in FIG. 10, the level of sleepiness of a driver can be indicated in a different way than the warning displayed in step S3. In the display of FIG. 10, the system controller 1 reads out, as shown in FIG. 11, the sleepiness evaluation value Pn and the location of the vehicle at a current time, the sleepiness evaluation value Pn and the location of the vehicle at a time of a predetermined period X (e.g., ten minutes) before the current time, and the sleepiness evaluation value Pn and the location of the vehicle at a time of a predetermined period 2X before the current time point (step S71), and further reads the sleepiness evaluation threshold value SN (step S72). The controller 1 then creates a red zone frame corresponding to the sleepiness evaluation threshold value SN (step S73), and then defines the size of a circle in the red zone for each of the current sleepiness evaluation value Pn, the sleepiness evaluation value Pn at the time of X before the current time, and the sleepiness evaluation value Pn at the time of 2X before the current time, thereby creating display data (step S74). As shown in FIG. 12, the size of a circle increases in the central portion of the red zone frame as the sleepiness evaluation value Pn increases. The system controller 1 acquires the current locations of other vehicles and the sleepiness evaluation value Pn via the vehicle-to-vehicle wireless communication device 5 (step S75), and then creates display data (step S76). Thereafter, the system controller 1 supplies, to the display device 6, the display data of its own vehicle created in step S74 and the display data of the other vehicles created in step S76 in conjunction with their respective location data (step S77). The display device 6 then processes the supplied display data for display and then superimposes the resulting data as shown in FIG. 10 on the map indicated by the map data from the navigation device 2. For example, on the map displayed, the sleepiness evaluation value Pn at the time of 2X before the current time is displayed at the self-location of the vehicle at the time of 2X before the current time on the traveled path as a marker 71 having a circular size corresponding to a sleepiness level 1. Also displayed is the sleepiness evaluation value Pn at the time of X before the current time at the self-location of the vehicle at the time of X before the current time as a marker 72 having a circular size corresponding to a sleepiness level 2, with the current sleepiness evaluation value Pn displayed at the current location of the vehicle as a marker 73 having a circular size corresponding to a sleepiness level 3. Furthermore, the current locations of the other vehicles are indicated with markers 74, 75 in other shapes. The markers 74, 75 may be different in shape from driver to driver as shown in FIG. 10 or shaped corresponding to the level of sleepiness.

The markers of the vehicle itself and other vehicles are not limited to the aforementioned examples, e.g., the current mental condition information evaluation value or the evaluation threshold value such as for sleepiness levels may also be indicated in accordance with not only the size of markers but also the color or pattern thereof. On the other hand, the shape or the like of the markers may be changed depending on the mental condition such as sleepiness, fatigue, and irritation.

As described above, in the window shown in FIG. 10, the driver's mental conditions of the vehicle itself and other vehicles can be displayed in conjunction with information on their respective locations, however, when the sleepiness or the like of the driver has been detected, the nearest service area may be displayed, followed by a navigational operation performed at the same time.

The present invention has been described with reference to, but not limited to, the case where the driver's sleepiness is determined, however, another mental condition such as fatigue, strain, and irritation may also be determined. Furthermore, the physiological data is not limited to the heartbeat rate of the driver, but other physiological data such as fluctuations in heartbeat, respiratory rate, and blood pressure may also be detected.

Figure 13:
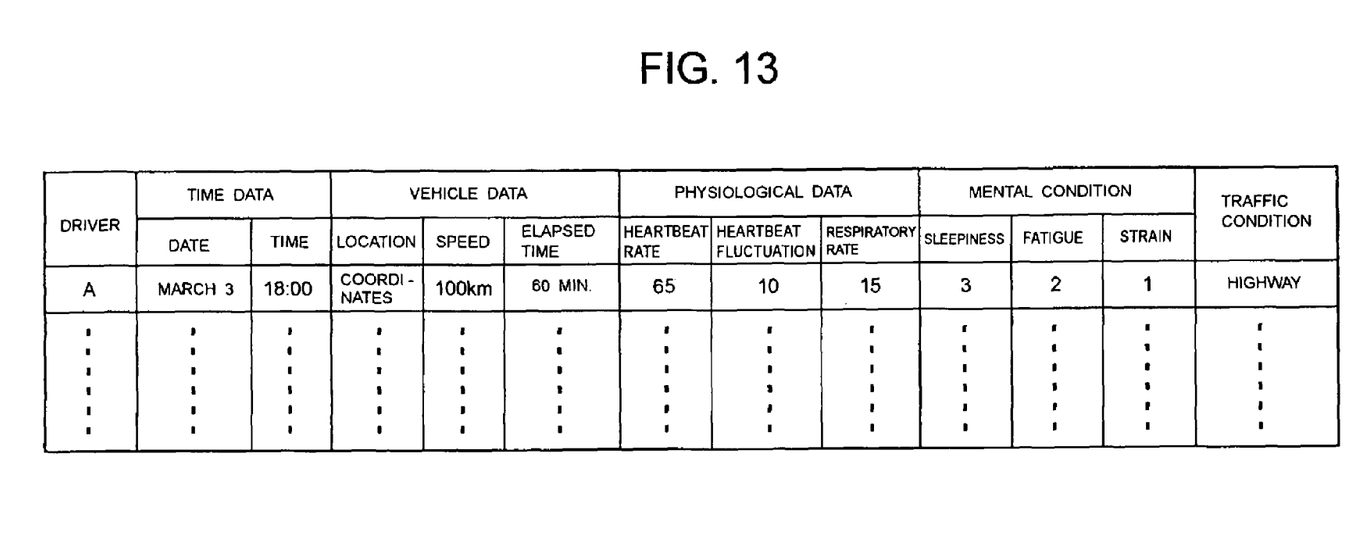
FIG. 13 is a view showing the structure of a database.
Figure 14:
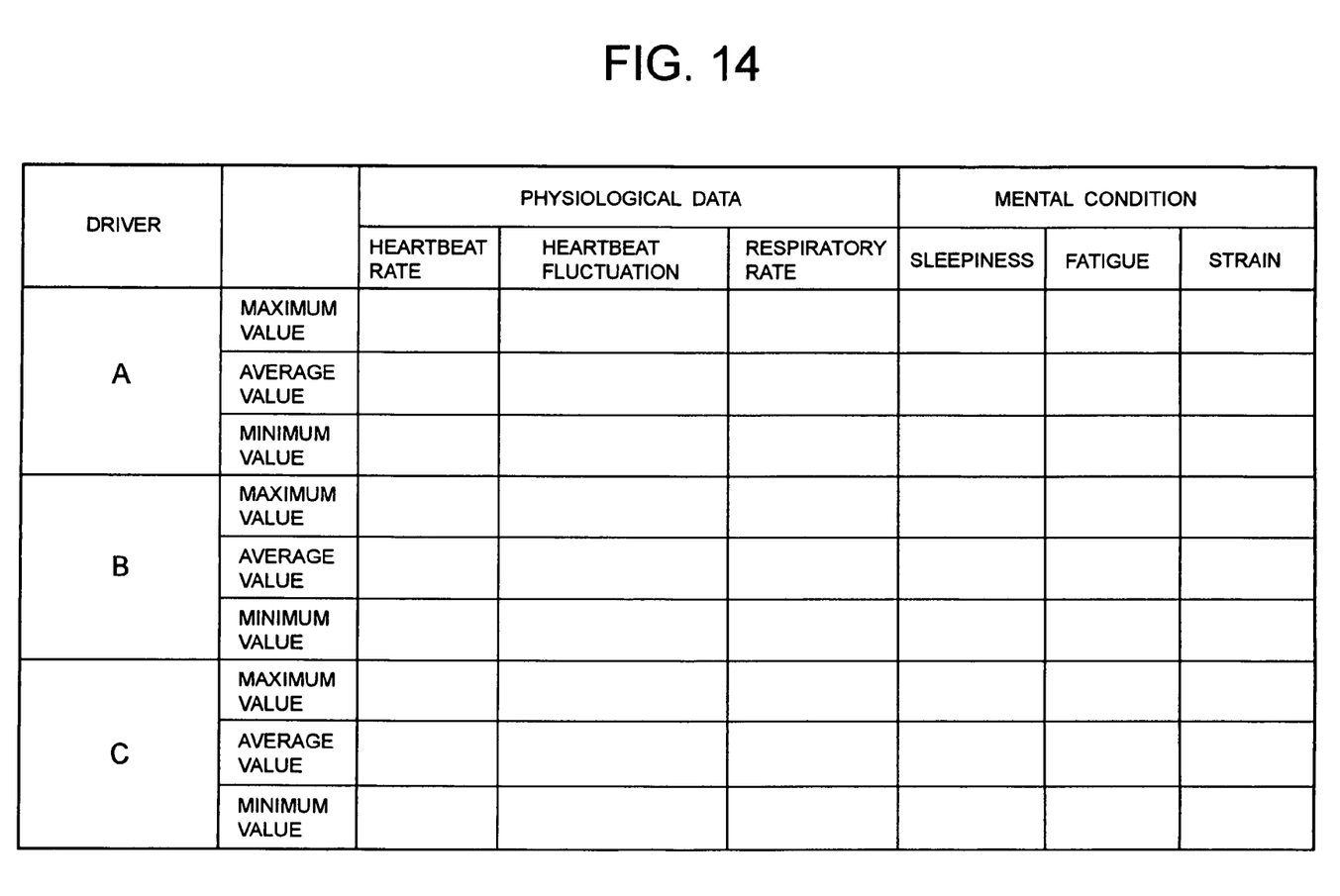
FIG. 14 is a view showing the structure of a database.

For example, in the aforementioned memory 9, the database as shown in FIG. 13 is formed when various types of vehicle data and physiological data are detected and various types of mental conditions are determined. As shown in FIG. 14, the physiological data and the mental condition are stored in a database with the maximum value, an average value, and the minimum value.

In the aforementioned embodiment, information on changes in mental condition is visually presented to the driver; however, the information on changes in mental condition may also be presented with variations in sound (e.g., changes in frequency of the sound generated).

As described above, the system according to the present invention comprises an evaluation threshold value setting device which sets a threshold value for evaluating the mental condition of a driver and an indicator which indicates the mental condition of the driver using a mental condition evaluation value in conjunction with the evaluation threshold value, thereby making it possible to precisely inform of the mental condition of the driver of a vehicle.

This application is based on a Japanese Patent Application No. 2002-188285 which is hereby incorporated by reference.

What is claimed is:

1. A driver mental condition information system comprising:
   a physiological data detector which detects physiological data of a driver of a vehicle,
   a mental condition calculator which calculates a mental condition of the driver as a mental condition evaluation value in accordance with the physiological data,
   an evaluation threshold value setting device which sets a threshold value for evaluating the mental condition of the driver, and
   an indicator which indicates the mental condition of the driver using the mental condition evaluation value along with the threshold value,
   a mental condition evaluation device which compares the mental condition evaluation value with the threshold value to evaluate the mental condition of the driver, and
   a self-location detector which detects a self-location of the vehicle,
   wherein said indicator displays the mental condition of the driver as a warning and further indicates a nearest service area when the mental condition of the driver is detected as a predetermined condition by said mental condition evaluation device.

2. A driver mental condition information system according to claim 1, further comprising
   a storage device which sequentially stores the mental condition evaluation value calculated by said mental condition calculator,
   wherein said indicator indicates a variation in mental condition of the driver using the mental condition evaluation value stored in said storage device along with the threshold value.

3. A driver mental condition information system according to claim 1, further comprising
   a driver identifying device which identifies a driver of the vehicle,
   wherein said evaluation threshold value setting device is allowed to set the threshold value at a desired value for each driver identified by said driver identifying device, and
   said indicator indicates the mental condition evaluation value of the driver along with the threshold value corresponding to the driver identified by said driver identifying device.

4. A driver mental condition information system according to claim 1, wherein said evaluation threshold value setting device has an adjuster for adjusting the threshold value in response to an input operation.

5. A driver mental condition information system according to claim 2, wherein said storage device has a database for storing physiological data, the mental condition evaluation value, and the threshold value for each driver.

6. A driver mental condition information system comprising:
   a physiological data detector which detects physiological data of a driver of a vehicle,
   a mental condition calculator which calculates a mental condition of the driver as a mental condition evaluation value in accordance with the physiological data,
   an evaluation threshold value setting device which sets a threshold value for evaluating the mental condition of the driver, and
   an indicator which indicates the mental condition of the driver using the mental condition evaluation value along with the threshold value.
   a self-location detector which detects a self-location of the vehicle, and
   a navigation device for outputting display map data indicative of a map including the self-location of the vehicle detected by said self-location detector, wherein said indicator displays a map in accordance with the display map data, and displays the mental condition evaluation value of the driver at each point on a travel path corresponding to the self-location detected by said self-location detector on the map displayed.

7. A driver mental condition information system according to claim 6, wherein
said indicator displays the threshold value along with the mental condition evaluation value displayed on said display map.

8. A driver mental condition information system according to claim 6, wherein
said indicator displays the mental condition evaluation value of the driver at each point on said travel path as a variation in shape size, color, or pattern.

9. A driver mental condition information system according to claim 6, further comprising
a vehicle-to-vehicle wireless communication device which collects, by radio waves, a location and a mental condition evaluation value of a driver of another vehicle near the vehicle, wherein
said indicator displays the mental condition evaluation value of the driver of the other vehicle at a position of said display map corresponding to the location of the other vehicle collected by said vehicle-to-vehicle wireless communication device.

10. A driver mental condition information system according to claim 6, wherein
when a mental condition of the driver is detected as a predetermined condition by said mental condition evaluation device, said indicator indicates a nearest service area and executes a navigational guidance operation for leading to the service area.

11. A method for displaying a driver's mental condition comprising:
detecting physiological data of a driver of a vehicle,
calculating a mental condition of the driver as a mental condition evaluation value in accordance with the physiological data,
setting a threshold value for evaluating of the mental condition of the driver, and
indicating the mental condition of the driver using the mental condition evaluation value along with the threshold values,
comparing the mental condition evaluation value with the threshold value to evaluate the mental condition of the driver, and
detecting a self-location of the vehicle,
wherein when the mental condition of the driver is detected as a predetermined condition, the mental condition of the driver is displayed as a warning and further a nearest service area is indicated in the indicating step.

12. A method for displaying a driver's mental condition, comprising the steps of:
detecting physiological data of a driver of a vehicle,
calculating a mental condition of the driver as a mental condition evaluation value in accordance with the physiological data,
setting a threshold value for evaluating of the mental condition of the driver,
indicating the mental condition of the driver using the mental condition evaluation value along with the threshold value,
comparing the mental condition evaluation value with the threshold value to evaluate the mental condition of the driver,
detecting a self-location of the vehicle, and
outputting display map data indicative of a map including the detected self-location of the vehicle,
wherein in the indicating step, a map is displayed in accordance with the display map data, and further the mental condition evaluation value of the driver is displayed at each point on a travel path corresponding to the detected self-location on the map displayed.

* * * * *